(12) United States Patent
Hansmann et al.

(10) Patent No.: US 11,964,108 B2
(45) Date of Patent: Apr. 23, 2024

(54) PROCESS AND DEVICE FOR VENTILATING A PATIENT

(71) Applicant: Drägerwerk AG & Co. KGaA, Lübeck (DE)

(72) Inventors: Hans-Ullrich Hansmann, Barnitz (DE); Karsten Hiltawsky, Stockelsdorf (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 783 days.

(21) Appl. No.: 16/755,011

(22) PCT Filed: Oct. 1, 2018

(86) PCT No.: PCT/EP2018/076564
§ 371 (c)(1),
(2) Date: Apr. 9, 2020

(87) PCT Pub. No.: WO2019/072605
PCT Pub. Date: Apr. 18, 2019

(65) Prior Publication Data
US 2020/0345962 A1    Nov. 5, 2020

(30) Foreign Application Priority Data

Oct. 13, 2017    (DE) ...................... 10 2017 009 602.3

(51) Int. Cl.
*A61M 16/20*    (2006.01)
*A61B 5/00*    (2006.01)
(Continued)

(52) U.S. Cl.
CPC ......... *A61M 16/204* (2014.02); *A61B 5/0836* (2013.01); *A61B 5/091* (2013.01);
(Continued)

(58) Field of Classification Search
CPC ............ A61M 16/204; A61M 16/0051; A61M 16/0057; A61M 16/024; A61M 16/06;
(Continued)

(56) References Cited

U.S. PATENT DOCUMENTS 6,976,487 B1    12/2005    Melker et al.
9,180,266 B1    11/2015    Sherman et al.
(Continued)

FOREIGN PATENT DOCUMENTS

CN    105828859 A    8/2016
CN    106714882 A    5/2017
(Continued)

*Primary Examiner* — Elliot S Ruddie
(74) *Attorney, Agent, or Firm* — McGlew and Tuttle, P.C.

(57) ABSTRACT

A process for ventilating a patient as well as a device—patient module (20)—operating according to the process, wherein, for example, a body weight value concerning an estimated body weight of the patient is transmitted to a patient module (20) intended for ventilating the patient, wherein the patient module (20) automatically selects ventilation parameters (52) fitting the body weight value on the basis of the body weight value and wherein the ventilation of the patient is carried out with the selected ventilation parameters (52).

5 Claims, 12 Drawing Sheets

(51) Int. Cl.
*A61B 5/083* (2006.01)
*A61B 5/091* (2006.01)
*A61M 16/00* (2006.01)
*A61M 16/06* (2006.01)
*A61M 16/08* (2006.01)
*A61M 16/10* (2006.01)
*F04B 45/047* (2006.01)
*F16K 31/00* (2006.01)
*F16K 31/126* (2006.01)

(52) U.S. Cl.
CPC ......... *A61B 5/746* (2013.01); *A61M 16/0051* (2013.01); *A61M 16/0057* (2013.01); *A61M 16/024* (2017.08); *A61M 16/06* (2013.01); *A61M 16/0833* (2014.02); *A61M 16/205* (2014.02); *F04B 45/047* (2013.01); *F16K 31/004* (2013.01); *F16K 31/1266* (2013.01); *A61M 2016/0036* (2013.01); *A61M 16/0063* (2014.02); *A61M 16/0066* (2013.01); *A61M 2016/103* (2013.01); *A61M 2205/0294* (2013.01); *A61M 2205/073* (2013.01); *A61M 2205/078* (2013.01); *A61M 2205/52* (2013.01); *A61M 2205/609* (2013.01); *A61M 2205/8206* (2013.01); *A61M 2205/84* (2013.01)

(58) Field of Classification Search
CPC ............ A61M 16/0833; A61M 16/205; A61M 16/0063; A61M 16/0066; A61M 2016/0036; A61M 2016/103; A61M 2205/0294; A61M 2205/073; A61M 2205/078; A61M 2205/52; A61M 2205/609; A61M 2205/8206; A61M 2205/84; A61M 16/0072; A61M 16/0078; A61M 16/127; A61M 2016/0027; A61M 2205/07; A61M 2205/3592; A61M 2205/502; A61M 2205/505; A61M 2205/6018; A61M 2205/825; A61M 2230/432; A61M 16/206; A61B 5/0836; A61B 5/091; A61B 5/746; A61B 5/082; A61B 5/087; F04B 39/102; F04B 2203/0404; F04B 53/10; F04B 45/047; F16K 7/01; F16K 31/004; F16K 31/1266; G08B 21/02; G16H 20/40; G16H 40/63
See application file for complete search history.

(56) References Cited

U.S. PATENT DOCUMENTS

| | | |
|---|---|---|
| 2002/0185127 A1 | 12/2002 | Melker et al. |
| 2011/0186050 A1 | 8/2011 | Daly |
| 2011/0232640 A1 | 9/2011 | Van Dijk et al. |
| 2012/0000470 A1 | 1/2012 | Milne et al. |
| 2013/0047989 A1 | 2/2013 | Vandine et al. |
| 2013/0167843 A1* | 7/2013 | Kimm ................. A61M 16/209 128/205.24 |
| 2013/0186394 A1* | 7/2013 | Hallett ............. A61M 16/0057 128/205.24 |
| 2015/0328417 A1* | 11/2015 | Löser ................ A61M 16/024 128/204.23 |
| 2017/0209665 A1 | 7/2017 | Acker et al. |

FOREIGN PATENT DOCUMENTS

| | | |
|---|---|---|
| EP | 2368592 A1 | 9/2011 |
| WO | 2014095962 A1 | 6/2014 |
| WO | 2016134999 A | 9/2016 |

* cited by examiner

PROCESS AND DEVICE FOR VENTILATING A PATIENT

CROSS REFERENCE TO RELATED APPLICATIONS

This application is a United States National Phase Application of International Application PCT/EP2018/076564, filed Oct. 1, 2018, and claims the benefit of priority under 35 U.S.C. § 119 of German Application 10 2017 009 602.3, filed Oct. 13, 2017, the entire contents of which are incorporated herein by reference.

TECHNICAL FIELD

The present invention pertains to a process for ventilating at least one patient as well as to a device intended for carrying out the process.

TECHNICAL BACKGROUND

Devices for ventilating a patient are, for example, ventilators or anesthesia devices. Ventilators and anesthesia devices—hereinafter summarily called ventilators or a ventilator in case of a single device—are used to provide breathing air for patients who either cannot breathe independently at all or require assistance during breathing. The patients wear for this purpose, for example, a face mask, which covers the mouth and the nose. The face mask or the like is connected to the ventilator via at least one ventilation tube.

Contrary to ventilators used in routine clinical practice, so-called emergency ventilators are known as well, which are set and operated for ventilating emergency patients, for example, by a trained emergency physician or a trained paramedic. If such a device is not available or not yet available at the location of a necessary emergency treatment, ventilation is frequently carried out by the first responders at the site with a breathing bag or a mask. Such breathing bags are inexpensive, can be stored and are ready to operate in a simple manner and immediately. Such breathing bags therefore belong to the standard equipment of rescue vehicles as well as vehicles of the fire department.

Data, which make it possible to obtain information concerning the success of ventilation (monitoring), are usually unavailable during a ventilation by means of a breathing bag. However, the operation of a breathing bag requires a great deal of experience and know-how in order to supply the emergency patient with a necessary respiration rate, reasonable airway pressures and with the correct tidal volume. Errors, which may subsequently lead to longer therapy times or even to permanent damage, may easily be made in such cases in a stress situation, which usually arises for a first responder at the location of an emergency.

Ventilators that allow an adequate ventilation are comparatively expensive and are only available, as a rule, in connection with the arriving emergency physician. In addition, the setting and operation of such a ventilator requires at least a training and such a ventilator can therefore usually only be operated by professionally trained staff with the rapidity that is required precisely in emergency situations.

SUMMARY

One object of the present invention is to propose a process for ventilating a patient and a device operating according to the process, which can also be operated by staff not trained medically or with minimal training, at least to the extent that an initial ventilation of the patient can be carried out.

This object is accomplished according to the present invention by means of a process for ventilating at least one patient according to the invention. Provisions are made for this purpose in the process being proposed here for ventilating a patient for an estimated value related to a biometric feature of the patient to be transmitted to a device intended for ventilating the patient, which acts as a ventilator and will hereinafter be called a patient module; for the patient module to select automatically ventilation parameters fitting the estimated value on the basis of the estimated value; and for the ventilation of the patient to be carried out at least initially with the automatically selected ventilation parameters.

With respect to the device, the above-mentioned object is accomplished by means of a device hereinafter called patient module for ventilating a patient, which has the features of the parallel device claim. The device, i.e., the patient module, is characterized in that an estimated value concerning an estimated biometric feature of the patient can be transmitted to this device or patient module; that ventilation parameters fitting the estimated value or at least a ventilation parameter fitting the estimated value can be automatically selected by means of the device or by means of the patient module on the basis of the estimated value; and that the ventilation of the patient is carried out with the selected ventilation parameter or with the selected ventilation parameters by means of the device or of the patient module.

The body dimensions of the patient, i.e., the body weight or the height of the patient, are considered to be biometric features. The following description will be continued, in the interest of better readability, but without abandoning a further general validity, on the basis of the example of an estimated body weight of the patient. An estimate height will always be implied. Provisions may also be made for body dimensions/body weight and height to be used together. By internal processing, the patient module can now automatically recognize input errors if the height and the body weight fail to clearly match.

The advantage of the solution being proposed here is that the necessity to set the patient module acting as a ventilator is reduced to a minimum. The input of an estimated body weight of the patient to be ventilated is sufficient for the patient module to be put into operation and for the ventilation of the patient to be able to begin. The ventilation parameters that are automatically selected on the basis of the inputted body weight value and are used at least initially during the ventilation of the patient include especially a tidal volume, a respiration rate, an inspiratory ventilation pressure, a pressure limiting and the so-called PEEP (positive end-expiratory pressure). Not all ventilation parameters are necessarily dependent on the inputted body weight value and may therefore be implemented as at least initial and body weight value-independent ventilation parameters. At least one ventilation parameter coding the tidal volume depends on the inputted body weight value and is obtained, for example, at 8 mL per kg of the inputted body weight value.

It may be assumed that less well-trained first responders can also ensure a ventilation of an emergency patient with this possibility of operating a patient module acting as a ventilator, at least until the arrival of medically trained staff, for example, an emergency physician. At any rate, it can be assumed that inhibitions resulting from concerns about the possibility of a possibly incorrect operation of the patient module acting as a ventilator are markedly lowered and that the risk that an at least initial emergency ventilation, which is basically possible, will be omitted because of ignorance or anxiety is thus avoided.

References used within the claims point to the further configuration of the subject of the claim being referred to by the features of the respective dependent claim. The references shall not be considered to represent abandonment of the wish to achieve an independent, concrete protection for the features or combinations of features of a dependent claim. Furthermore, it shall be assumed in respect to an interpretation of the claims as well as of the description in case of a closer concretization of a feature in a dependent claim that such a limitation is not present in the respective preceding claims as well as in a more general embodiment of the concrete patient module. Any reference in the description to aspects of dependent claims shall accordingly expressly imply a description of optional features even without a special reference.

Provisions are made in embodiments of the process, which are explained below, for an automatic adaptation of the ventilation parameters that are selected automatically on the basis of the inputted body weight value and are used at least initially to be carried out. At least individual ventilation parameters, on the basis of which the automatic ventilation of the patient is carried out by means of the patient module, are thus variable and differ after a certain duration of ventilation from the ventilation parameters selected automatically on the basis of the inputted body weight value. This shall always be taken into consideration below when referring to the automatically selected ventilation parameters.

A $CO_2$ measured value is determined by means of a sensor mechanism, especially by means of at least one $CO_2$ sensor, during the ventilation of the patient in one embodiment of the process. The $CO_2$ concentration in the exhaled breathing gas, which concentration is known to be increased during a phase of exhalation, so that a $CO_2$ measured value in the range of an elevated $CO_2$ expected measured value ($CO_2^{ex}$) is expected, can be monitored by means of the $CO_2$ measured value. The $CO_2$ expected measured value is, for example, above a $CO_2$ measured value recorded during the phase of inhalation by about 3-5 vol.%, especially above a mean value of a plurality of $CO_2$ measured values recorded during the phase of inhalation by about 3-5 vol. %. If the $CO_2$ expected measured value is not reached during a phase of exhalation, an alarm is triggered automatically. The $CO_2$ expected measured value seen during a phase of exhalation is optionally updated continuously on the basis of at least one $CO_2$ measured value during a preceding phase of inhalation. The alarm may be triggered in the form of an automatic actuation of an optical and/or acoustic signal element comprised by the patient module. The first responder is alerted by the triggering of an alarm that the ventilation of the patient is not functioning as expected or that the metabolism or the circulation of the patient is not working correctly. The first responder may then at least check whether, for example, a face mask has been placed correctly over the mouth and the nose of the patient and/or whether a ventilation tube leading to the patient module has possibly become detached.

An inhalation volume fed during a phase of inhalation and an exhalation volume exhaled during a phase of exhalation are determined by means of a sensor mechanism, especially by means of at least one flow sensor, in an additional or alternative embodiment of the process, a difference between the inhalation volume and the exhalation volume is compared to a preset or presettable limit value, and an alarm is triggered when the limit value is exceeded. Possible leaks can be recognized automatically by means of the patient module by the monitoring of the difference between the inhalation volume and the exhalation volume. An alarm triggered, for example, by means of an automatic actuation of an optical and/or acoustic signal element comprised by the patient module indicates to the first responder that the ventilation is not yet functioning properly and that, for example, a face mask shall be checked for correct fitting.

Provisions may optionally be made in all the alarms mentioned here and hereinafter, which are triggered automatically by the patient module, in case of a display element comprised by or associated with the patient module, for example, a display element in the form of a display screen, an LCD display or the like, for outputting a message fitting the particular alarm situation, especially in the form of a text message, with instructions for actions for the first responder. For example, a message, which prompts checking of the face mask for correct fitting, may thus be outputted in case of an excessively great difference between the inhalation volume and the exhalation volume. A message in the form of a text message may optionally be outputted simultaneously or alternatingly in different languages. The message may also be outputted, in addition or as an alternative to a message in the form of a text, in the form of pictograms or the like.

The $CO_2$ expected measured value ($CO_2''$) is reduced as a function of the difference between the inhalation volume and the exhalation volume in an optional embodiment of the process. A simple example may illustrate this: When a measured inhalation volume equals 1 L, while the exhalation volume is only 0.5 L, a leak can be assumed. Such a leak will usually be distributed linearly over the airway pressure. A simple assumption is a constant leak. A gas flow over the inhalation valve, which reduces the $CO_2$ content, is necessary now for maintaining a PEEP pressure in case of such a large leak (0.25 L/breath): $CO_2^{ex} = CO_2^{actual}/(0.5/0.5+0.25)$.

A measured tidal volume is determined in an additional or alternative embodiment of the process during the ventilation of the patient by means of a sensor mechanism, especially by means of at least one flow sensor, for example, by integrating a measured value that can be obtained from a flow sensor. An inspiratory ventilation pressure effective during the ventilation of the patient is automatically increased in case of a measured tidal volume lower than the preset tidal volume resulting on the basis of the automatically determined ventilation parameter and the inspiratory ventilation pressure is correspondingly automatically reduced in case of a measured tidal volume greater than the preset tidal volume. The ventilation and the ventilation parameters, including the inspiratory ventilation pressure, are automatically adapted in this manner to the respective conditions. A possibly incorrectly estimated body weight value and initially used ventilation parameters, which result therefrom and which do not yet fit optimally, are thus essentially noncritical and the patient module fits the automatic ventilation independently in a physiologically meaningful manner. The automatic increase or decrease of the inspiratory ventilation pressure with a preset or presettable increment optionally takes place such that the inspiratory ventilation pressure is increased or reduced corresponding to the increment as needed in each ventilation cycle. Preset or presettable limit values, for example, 25 mbar or PEEP+5 mbar, which cannot be exceeded or fallen below in case of a possible stepwise increase or reduction of the inspiratory ventilation pressure, are optionally programmed as well.

In an additional or alternative embodiment of the process, a ventilation rate effective during the ventilation of the patient is lowered during the ventilation of the patient with the ventilation parameters that were selected automatically on the basis of the inputted body weight value and were used at least initially if it is found on the basis of a measured tidal volume that the preset tidal volume is not reached. Provisions are optionally made for the ventilation rate effective during the ventilation of the patient to be lowered if a preset or presettable upper limit value is reached for the ventilation pressure on the basis of a measured tidal volume below the preset tidal volume.

In an additional or alternative embodiment of the process, a volume flow measured value is detected by means of a sensor mechanism, especially by means of a flow sensor, during the ventilation of the patient with the ventilation parameters selected automatically on the basis of the inputted body weight value and used at least initially and a duration of a pause in breathing between a phase of inhalation and a subsequent phase of exhalation is determined on the basis of the volume flow measured value. The determined duration of the pause in breathing is compared to a preset or presettable limit value, and an inspiratory ventilation pressure effective during the ventilation of the patient is lowered to protect the lungs of the patient. This lowering of the inspiratory ventilation pressure may also take place incrementally (from one breathing cycle to the next breathing cycle) at a preset or presettable increment.

At least one measured value determined by means of a sensor mechanism is recorded during the ventilation of the patient in an additional or alternative embodiment of the process. The recording optionally comprises a plurality of measured values, for example, $CO_2$ measured values, pressure and/or flow measured values. Such a recording makes the time course and a possible change over time in the at least one recorded measured value recognizable and makes it especially possible for a medically trained responder to assess the quality of the current ventilation subsequent to an initial emergency ventilation.

In another embodiment of the process, the body weight value is transmitted to the patient module intended for ventilating the patient by means of an operating unit connected to the patient module in a wireless manner, for example, to a smartphone acting as an operating unit or the like. An operating unit is not necessary in this case on the side of the patient module and the patient module may have an especially compact and inexpensive configuration. A computer program (app), which makes possible the input of a body weight value and the wireless transmission of a datum coding the body weight value to the patient module, is installed on the side of a smartphone acting, for example, as an operating unit, in a manner that is known per se. A smartphone or the like already comprises the communication devices necessary for the wireless transmission of the datum in question, and the datum is transmitted, for example, according to the NFC standard or according to the Bluetooth standard. Fitting communication devices, which are basically known per se and which make it possible to interpret a communication protocol and to receive a datum transmitted in a wireless manner, are provided on the side of the patient module.

On the whole, the innovation being proposed here is also a device having means for carrying out the process here and hereinafter described, namely, the device called patient module here.

In one embodiment of the device/patient module, which device/patient module couples a pressure source for flow with a patient interface that can be connected to the airways of a patient and can be detachably connected to the patient interface, the device/the patient module comprises either exactly one special valve device acting as an exhalation valve or a special valve device acting as an inhalation valve, on the one hand, and as an exhalation valve, on the other hand. The valve device or each valve device comprises a valve drive, a pressure chamber as well as a control pressure chamber, and the valve drive is connected to the control pressure chamber for generating a control pressure in the control pressure chamber. A piezo pump, which can preferably be operated at a high frequency, acts as a valve drive. The piezo pump acts on a closing element and a diaphragm element, the diaphragm element and the closing element separating the control pressure chamber from the pressure chamber. The closing element (the position of the closing element) can be controlled via the diaphragm element by means of the control pressure and a first opening of the pressure chamber can be opened and closed by means of the closing element, so that the valve function is obtained. The state of the valve device can be set rapidly and precisely by means of the valve drive and of the control pressure generated therewith during the operation.

In a special embodiment of the device/patient module, a valve device with back pressure control is provided as an inhalation valve. The valve device (the inhalation valve) comprises now a connection chamber belonging to the valve drive as well as a branch line element connecting the connection chamber to an outlet-side connection line element in a fluid-communicating manner. Depending on the flow direction, one of the two connection line elements of the valve device acts as an outlet or outlet-side connection line element. A pressure equalization is carried out by means of the branch line element between the control chamber and the outlet-side connection line element. This element receives the full working range (pressure range) of the valve drive, whereas the pressure exerted by the valve drive on the diaphragm (diaphragm element and closing element) would also have to overcome the possibly present back pressure without such a pressure equalization.

Since the patient module acts as an interface between a pressure source connected to its inlet side and a breathing mask for a patient or the like, which is connected to its outlet side, and it generates the pressure and volume flow conditions necessary for the ventilation of a patient on its outlet side independently as well as automatically from a pressure and volume flow present on the inlet side, a plurality of patient modules can be connected in parallel to a central pressure source. Another aspect of the innovation being presented here is thus a system with a central pressure source and with a plurality of patient modules of the type here and hereinafter described, which are connected to the pressure source. Such a system is considered for use, for example, in the case of an epidemic or the like, because a plurality of patients can be ventilated at the same time and because the operation of every individual patient module is simple, can be carried out without special training, and it does not require permanent supervision. Compared to a number of ventilators otherwise necessary for a simultaneous ventilation of a plurality of patients, such a system is associated with a considerably reduced amount of devices, so that the components comprised by such a system can be stocked better and above all in a more cost-effective manner.

The process here and hereinafter described for ventilating a patient is preferably embodied in the form of a computer program for being executed automatically. The present invention is thus also a computer program with program code instructions that can be executed in the form or in the manner of a microprocessor, on the one hand, and, on the other hand, a storage medium with such a computer program, i.e., a computer program product with program code means, as well as finally also a device for ventilating a patient, especially a device in the form of the patient module being described here, with such a processing unit and with a memory, into which such a computer program is or can be loaded as a means for executing the process and embodiments thereof.

Whenever process steps or process step sequences are here and hereinafter described, this refers, in case of an implementation of the process in software, to actions that take place on the basis of the computer program or under the control of the computer program, unless it is expressly pointed out that individual actions are prompted by a user of the computer program. At any rate, each use of the term "automatic" means that the action in question takes place on the basis of the computer program or under the control of the computer program.

Instead of in the form of a computer program, with individual program code instructions, the process here and hereinafter described may also be implemented in the form of firmware. It is clear to the person skilled in the art that an implementation in firmware or in firmware and software or in firmware and hardware is also always possible instead of an implementation of a process in software. The description being presented shall therefore imply that the term software or the terms control program and computer program also cover other possibilities of implementation, namely, especially an implementation in firmware or in firmware and software or in firmware and hardware.

An exemplary embodiment of the present invention will be explained in more detail below on the basis of the drawings. Mutually corresponding subjects or elements are designated by the same reference numbers in all figures.

The exemplary embodiment shall not be considered to represent a limitation of the present invention. Rather, variations and modifications, especially such variants and combinations which the person skilled in the art can find in respect to accomplishing the object, for example, by a combination or variation of individual features contained in the general or special text of the description as well in the claims and/or in the drawings and lead to a new subject by combinable features, are possible within the framework of the present disclosure. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
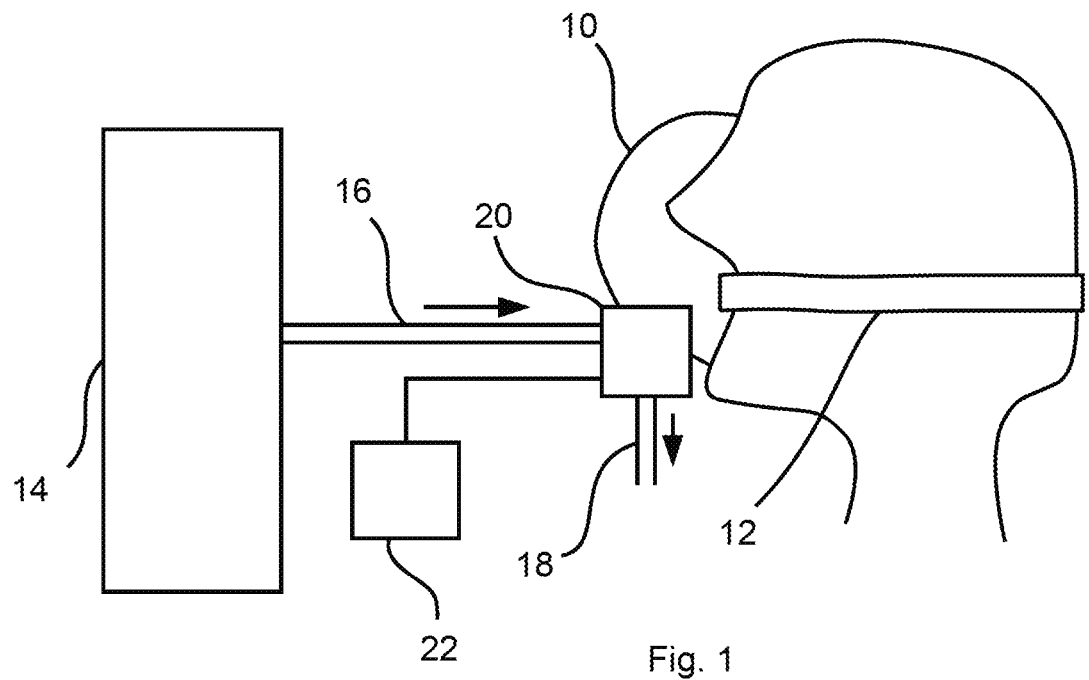
FIG. 1 is a schematic view of a patient ventilated by means of a pressure source and a patient module.

Referring to the drawings, the view in FIG. 1 shows, in a schematically highly simplified manner, a patient, who wears a breathing mask (ventilation mask) acting as a patient interface 10 for the ventilation. For example, a so-called tube (endotracheal tube) or an endotracheal cannula may also be considered, in principle, for use as a patient interface 10 instead of a breathing mask. The following description will be continued, without abandoning a further general validity, on the basis of the example of a breathing mask as a patient interface 10, which can be used incomparably more easily than a tube, since the innovation being proposed here shall also make possible, above all, the ventilation of a patient in an emergency situation, without having to presume a special experience of a first responder or the like for intubation or the like.

The patient wears the breathing mask over the mouth and nose in a manner that is basically known per se, and the breathing mask is held in this position, for example, by means of a strapping 12 or by the responder. The breathing mask/patient interface 10 is connected to a pressure source 14 in a manner that is basically known per se. The pressure source 14 is preferably a constant pressure source 14. A constant pressure source 14 is, for example, a pressurized gas cylinder, a gas feed unit for providing a constant gas pressure, e.g., a rotary compressor or a gas supply unit, e.g., a wall-mounted supply unit in a hospital.

At least one ventilation tube 16, especially exactly one ventilation tube 16, namely, at least one or exactly one ventilation tube 16 acting as an inhalation tube, which sends breathing gas from the pressure source 14 to the patient interface 10, leads for this purpose from the pressure source 14 to the patient interface 10.

One or more possible pressure reducers on the side of the pressure source 14 are not shown in the schematically simplified view in FIG. 1. The type and the number of possible pressure reducers depend on the pressure source 14 and the pressure prevailing there. Two pressure reducers are commonly used, namely, a first pressure reducer, which reduces the pressure to, for example, 5 bar, and a following second pressure reducer, which reduces the pressure to, for example, 500 mbar, in the case of a pressurized gas cylinder as a pressure source 14 containing breathing gas under a pressure of, for example, 440 bar.

The at least one ventilation tube 16 is connected on the side of the patient interface 10 to a patient module 20, which is connected to the patient interface 10 or acts as a coupling unit to the patient interface 10.

An operating unit 22, which is comprised by the patient module 20 or (as is shown) is independent from the patient module 20 and is connected to the patient module 20 in a communicating manner, is provided for the intended simple operation. Transmission of data from the operating unit 22 to the patient module 20 is possible in a manner basically known per se in the case of an operating unit 22 connected in a communicating manner to the patient module 20 in a wired or wireless manner, the transmitted data coding an input performed at the operating unit 22.

A responder inputs an estimated value concerning the body weight of the patient at the operating unit 22 for ventilating the patient. An additional input is not necessary. For example, a so-called smartphone or the like may also be considered for use as an operating unit 22.

Figure 2:
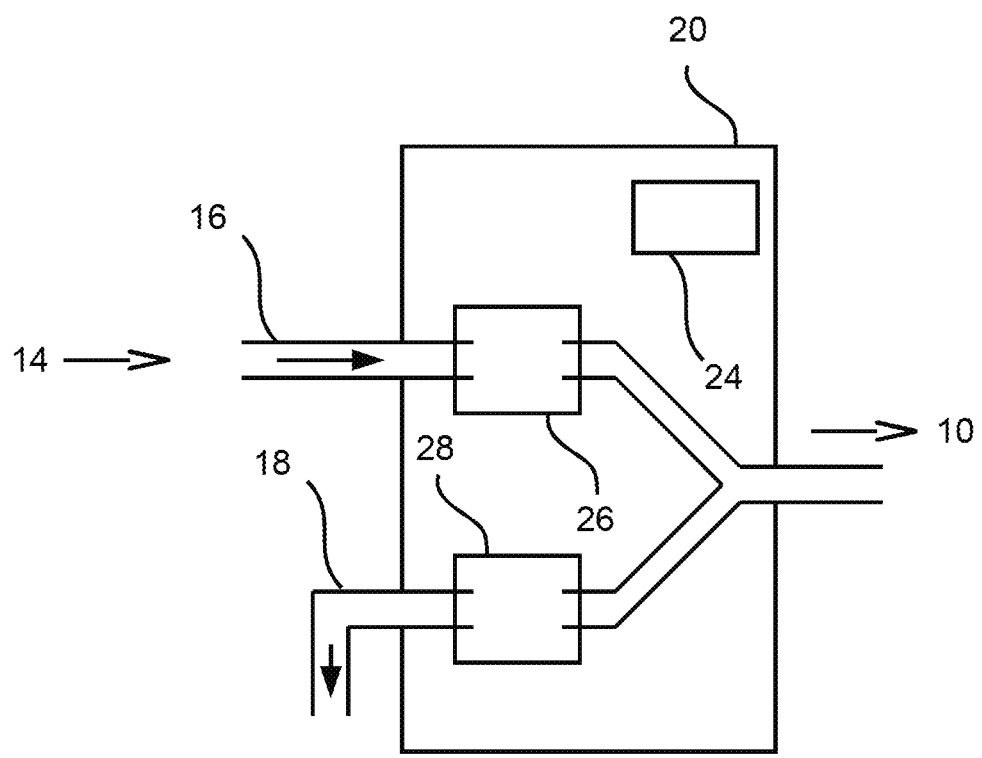
FIG. 2 is a schematic view of the patient module with further details, namely, at least one valve device comprised by the patient module.

The view in FIG. 2 shows the patient module 20—further simplified schematically—with further details. Thus, the patient module 20 comprises a valve device 30 acting as an inhalation valve 26 and as an exhalation valve 28 (FIG. 3, FIG. 5). The inhalation valve 26 is connected to the pressure source 14 via the ventilation tube 16. The exhalation valve 28 opens to the environment, and a (short) ventilation tube 18 open to the ambient pressure is optionally connected on the outlet side.

In the embodiment shown in FIG. 2, the patient module 20 comprises two valve devices 30, namely, an inhalation valve 26 and an exhalation valve 28. The inhalation or exhalation path connected to the respective valve 26, 28 is merged in the interior of the patient module 20 to a line to and from the patient interface 10 by means of a so-called Y-piece in the manner basically known per se. The inhalation valve 26 (with the exhalation valve 28 closed) is opened in a controlled or regulated manner during the inhalation phase and the volume flow coming from the pressure source 14 reaches the patient interface 10 via the Y-piece and enters the patient's lungs. The exhalation valve 28 (with the inhalation valve 26 closed) is opened in a controlled or regulated manner during the subsequent phase of exhalation and a pressure equalization takes place via the Y-piece and the exhalation valve 28 between the patient interface 10 and the environment and hence between the patient's lungs and the environment.

The patient module 20 minimally comprises, instead of two valve devices 30, exactly one valve device 30, namely, a valve device 30 acting as an exhalation valve 28, and it forms, together with the pressure source 14, a simple ventilator. The ventilation tube 16 coming from the pressure source 14 is then connected to the interior of the housing of the patient module 20 via a junction quasi replacing the non-existing inhalation valve. A Y-piece is likewise absent. The interior of the housing of the patient module 20 connects the junction to the ventilation tube 16, the line to and from the patient interface 10 and the exhalation valve 28 pneumatically to one another. The pressure source 14 delivers a volume flow with breathing gas under an overpressure relative to the ambient pressure, the volume flow preferably being constant. The ventilation of the patient can be carried out during the phase of inhalation by means of this volume flow in a manner basically known per se. The exhalation valve 28 opens in a controlled or regulated manner during the phase of inhalation as a function of the pressure coming from the pressure source 14 via the ventilation tube 16 and thus it possibly brings about a pressure reduction to a pressure that is necessary and acceptable for the inhalation. The exhalation valve 28 opens for pressure equalization to the environment during a phase of exhalation following the phase of inhalation and is likewise opened in the process in a controlled or regulated manner in a manner basically known per se for obtaining a pressure difference necessary for the exhalation relative to the pressure in the patient's lungs.

Figure 3A:
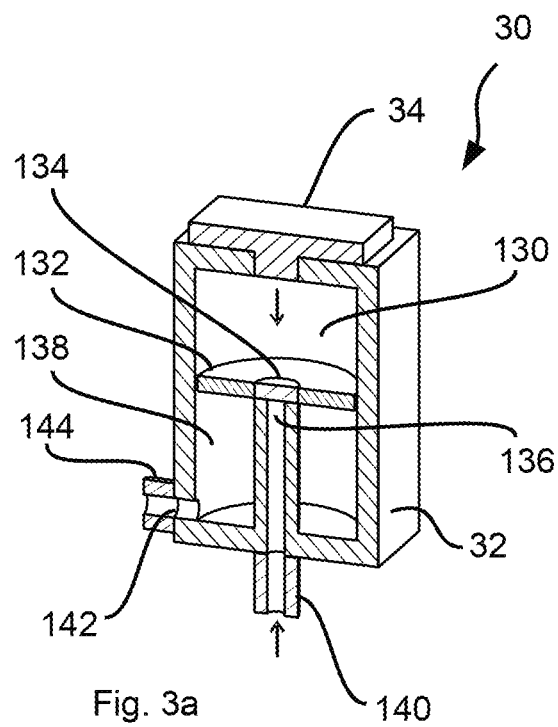
FIG. 3a is a sectional view of an embodiment of a valve device comprised by the patient module.
Figure 3B:
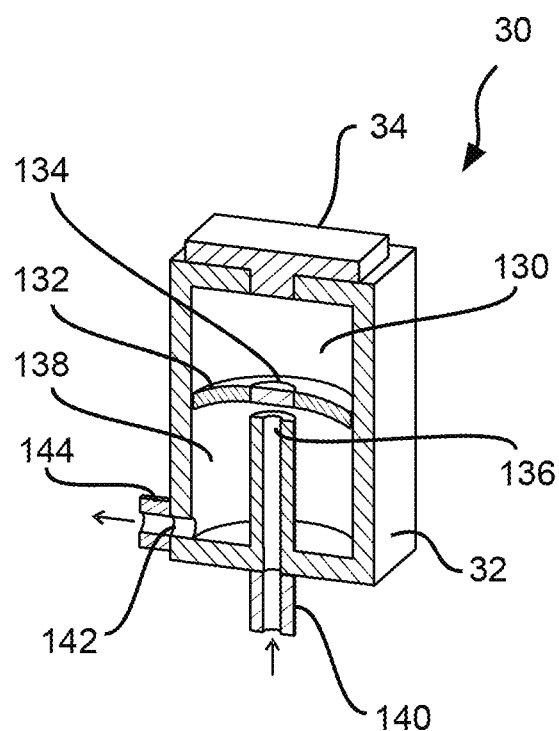
FIG. 3b is a sectional view of an embodiment of a valve device comprised by the patient module.

The views in FIG. 3 (FIGS. 3a, 3b) and in FIG. 5 (FIGS. 5a through 5d) show a valve device 30 acting as a pneumatic control device. The valve device 30 according to FIG. 3 is considered for use as an inhalation valve 26 and as an exhalation valve 28. The valve device 30 according to FIG. 5 is likewise considered for use as an inhalation valve 26. Each valve device 30 comprises a housing 32 and a pumping device connected to the housing 32 and acting as a valve drive 34. A piezo pump acts as a pumping device/valve drive 34. The pumping device/the piezo pump preferably has a flow in two directions and is consequently a two-way pump.

A valve device 30 may have more than one valve drive 34 (pumping device/piezo pump). The piezo pumps may be configured here as a stack of piezo pumps connected in series. The pump pressures of a plurality of piezo pumps can be combined by means of stacking. As an alternative, a plurality of piezo pumps connected in parallel may be present in the valve device 30.

Figure 4A:
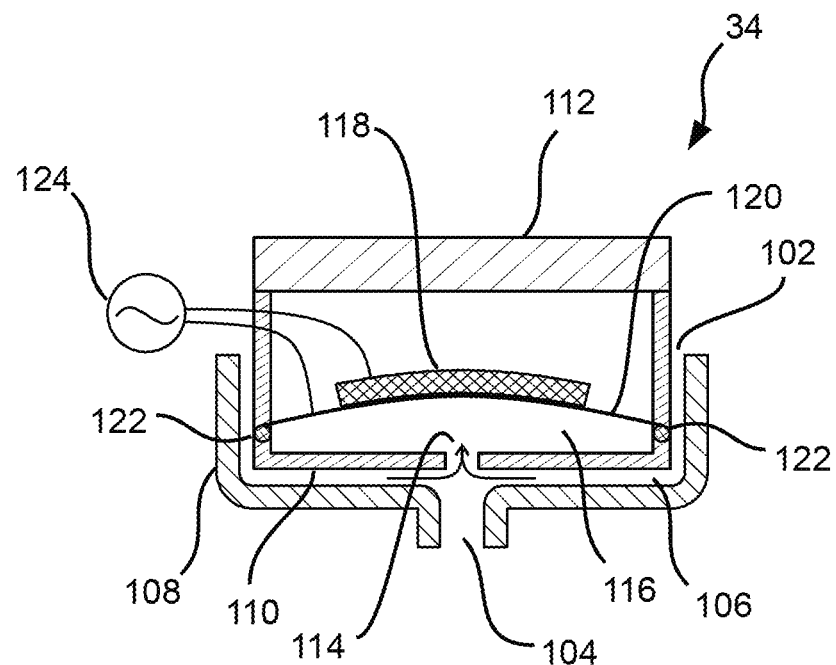
FIG. 4a is a sectional view of an embodiment of a valve drive of a valve device.
Figure 4B:
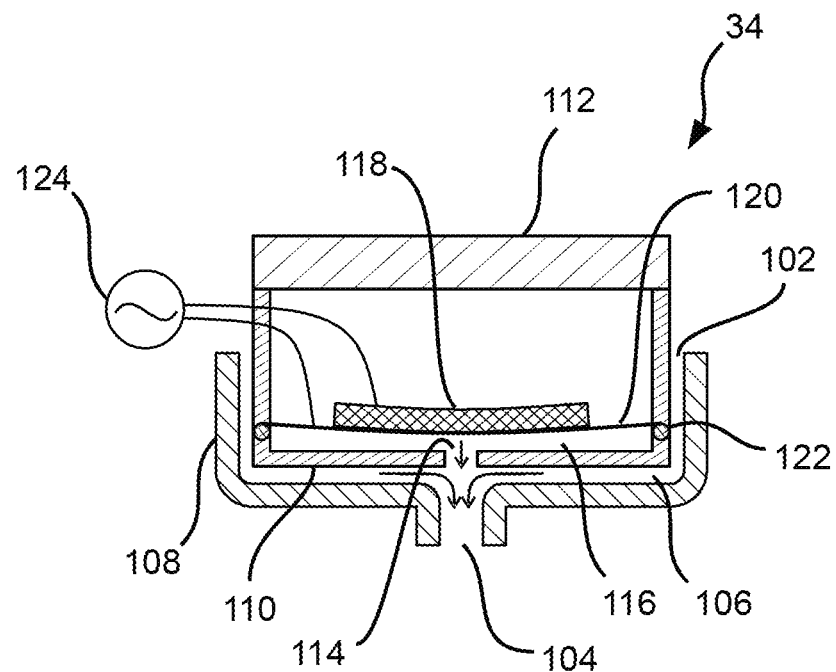
FIG. 4b is a sectional view of an embodiment of a valve drive of a valve device.

FIG. 4 (FIGS. 4a, 4b) shows the valve drive 34 with further details. Thus, the valve drive 34 has a first two-way passage opening 102 and a second two-way passage opening 104, which are connected by a two-way duct 106. The two-way duct 106 extends between an outer housing 108 and an inner housing 110. The second two-way passage opening 104 is formed in the outer housing 108. The first two-way passage opening 102 is obtained based on a distance between an edge of the outer housing 108 and the adjoining inner housing 110. The inner housing 110 is closed by means of a cover plate 112.

A pumping opening 114, which connects the two-way duct 106 to a pump chamber 116, is arranged in the inner housing 110 in the two-way duct 106. A piezo element 118 and a pump diaphragm element 120 are arranged in the pump chamber 116. The pump diaphragm element 120 is connected to the piezo element 118, on the one hand, and, via flexible connection elements 122, to the inner housing 110, on the other hand. The piezo element 118 is acted on with alternating electrical voltages in a manner known basically per se by means of an alternating voltage generator 124. These voltages bring about a voltage-induced deformation of the piezo element 118 and this deformation leads to a controlled vibration of the pump diaphragm element 120. Based on a preferably high-frequency alternating voltage sent by means of the alternating voltage generator, the pump diaphragm element 120 also vibrates in the pump chamber 116 with a preferably high frequency and pumping shocks are generated as a result by the resulting change in the volume of the pump chamber 116 (function of the piezo pump acting as a valve drive 34, preferably as a high-frequency pump). The action of these pumping shocks can propagate through the pumping opening 114 into the two-way duct 106 and bring about a flow of a particular fluid, for example, air, through the second two-way passage opening 104.

The flow through the pumping opening 114, which is directed out of the pump chamber 116, is directed towards the second two-way passage opening 104, i.e., a pumping shock, which is generated by a reduction of the volume of the pump chamber 116, is directed through the pumping opening 114 directly to the second two-way passage opening 104. The flow between the pumping opening 114 and the second two-way passage opening 104 carries with it the fluid in the two-way duct 106 in this case, so that a flow from the first two-way passage opening 102 to the second two-way passage opening 104 is generated. In case of an increase of the volume of the pump chamber 116, the fluid is sucked from the two-way duct 106 through the pumping opening 114 into the pump chamber 116. The fluid is sucked in this case from the two-way duct 106 into the pump chamber 116.

The pumping opening 114 is arranged at such a distance from the second two-way passage opening 104 that only a small percentage of fluid flows through the second two-way passage opening 104 into the two-way duct 106 through the pumping opening 114 into the pump chamber 116. The larger portion of the fluid is sucked into the pump chamber 116 from the first two-way passage opening 102 through the two-way duct 106 and the pumping opening 114. When the valve drive (piezo pump) 34 is switched off, there is no directed flow in the two-way duct 106. There rather is a free flow path now through the two-way duct 106, which may be directed in both directions, between the first two-way passage opening 102 and the second two-way passage opening 104. Thus, a pressure equalization can take place between the first two-way passage opening 102 and the second two-way passage opening 104. No relief valve or the like is therefore needed.

In the embodiment of the valve device 30 according to FIG. 3a, the valve drive 34 is configured and arranged to pump air from the environment into a control pressure chamber 130 in the interior of the housing 32 of the valve device 30. A pressure increase is consequently generated in the control pressure chamber 130 by means of the valve drive 34. The arrow pointing vertically downward under the valve drive 34 indicates here the control flow direction, with which a fluid flow is represented away from the valve drive 34 (out of the piezo pump). The valve drive 34 is connected to the control pressure chamber 130 in a fluid-communicating manner for generating a control pressure in the control pressure chamber 130.

Together with a closing element 134, a diaphragm element 132 forms an elastically movable wall of the control pressure chamber 130. The diaphragm element 132 is connected to the closing element 134, especially in one piece with the closing element 134. The closing element 134 is configured to close or to open a first opening 136 of a pressure chamber 138 formed in the interior of the housing 32. The diaphragm element 132 and the closing element 134 divide the interior of the housing 32 of the valve device 30 and separate the control pressure chamber 130 from the pressure chamber 138. The first opening 136 may have a diameter of 1 mm to 10 mm. The selected diameter of the first opening 136 depends on the admission pressure with which the pneumatic valve device 30 operates.

The diaphragm element 132 is deflected towards the opening 136 based on an increased pressure in the control pressure chamber 130 in the situation shown in FIG. 3a. The closing element 134 is pressed now onto the first opening 136 and the first opening 136 is closed. The diaphragm element 132 is deflected in the opposite direction and the first opening 136 is open in the situation shown in FIG. 3b.

If the valve device 30 according to FIG. 3 acts as an inhalation valve 26 in a patient module 20 (FIG. 2), the pressure source 14 (FIG. 1) is connected, for example, to a first connection line element 140, at the end of which the first opening 136 is located in the interior of the housing 32. The volume flow resulting from the pressure source 14 is represented by the vertically upwards pointing arrow, which is shown under the connection line element 140 and which indicates the flow direction in the pump. The pressure generated by the pressure source 14 at the first opening 136 is possibly insufficient to compensate the pressure generated by means of the valve drive 34 in the control pressure chamber 130. The closing element 134 correspondingly closes the first opening 136 until a control pressure whose force on the diaphragm element 132 is weaker than the force that acts on the diaphragm element 132 on the basis of the pressure source 14 is generated in the control pressure chamber 130 by means of the valve drive 34.

The pressure chamber 138 further has a second opening 142, which is joined by a second connection line element 144. The second connection line element 144 acts as an outlet to a patient or to the patient interface 10 (FIG. 1) in the case of a function as an inhalation valve 26 or to an environment in case of a function as an exhalation valve 28 ["sein" does not belong in the sentence—Tr.Ed.]. As long as the closing element 134 closes the first opening 136, no fluid flows through the second opening 142.

The view in FIG. 3b shows a situation as it arises with the valve drive 34 switched off. The valve drive 34 (the piezo pump) forms now an open fluid-communicating connection between the control pressure chamber 130 and the environment, i.e., a pressure equalization takes place between the control pressure chamber 130 and the environment, so that ambient pressure is present in the control pressure chamber 130. The pressure in the first connection line element 140 is higher now, for example, because of a connected pressure source 14 (FIG. 1), than the pressure in the control pressure chamber 130, which acts on the diaphragm element 132. The diaphragm element 132 with the closing element 134 is pushed now into the control pressure chamber 130, so that the closing element 134 opens the first opening 136. The first opening 136 and the second opening 142 are then connected to one another via the pressure chamber 138 in a fluid-communicating manner, so that a fluid can flow from the first opening 136 to the second opening 142 (and from the first connection line element 140 into the second connection line element 144). The resulting volume flow is illustrated by the arrow shown next to the second connection line element 144, which indicates the flow direction. The pneumatic valve device 30 is now opened.

Figure 5A:
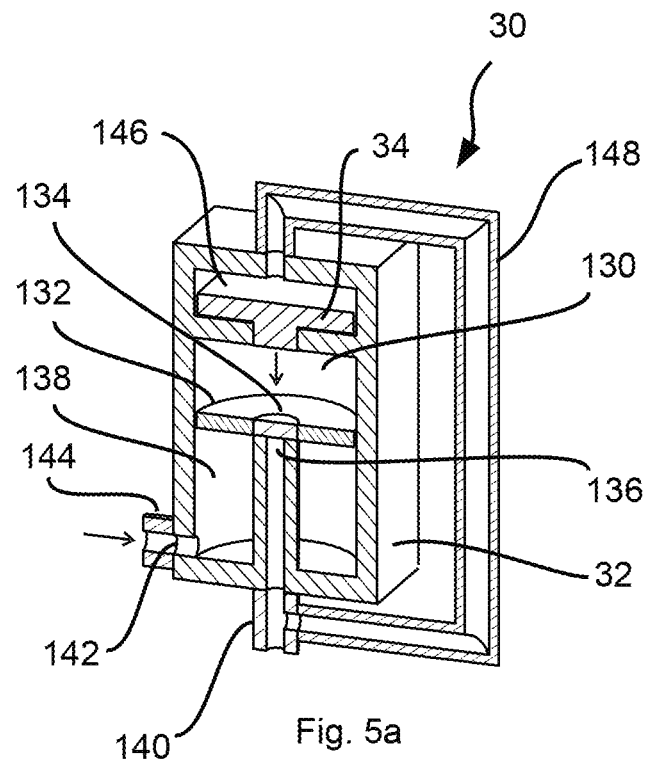
FIG. 5a is a sectional view of an alternative embodiment of a valve device according to FIG. 3.
Figure 5B:
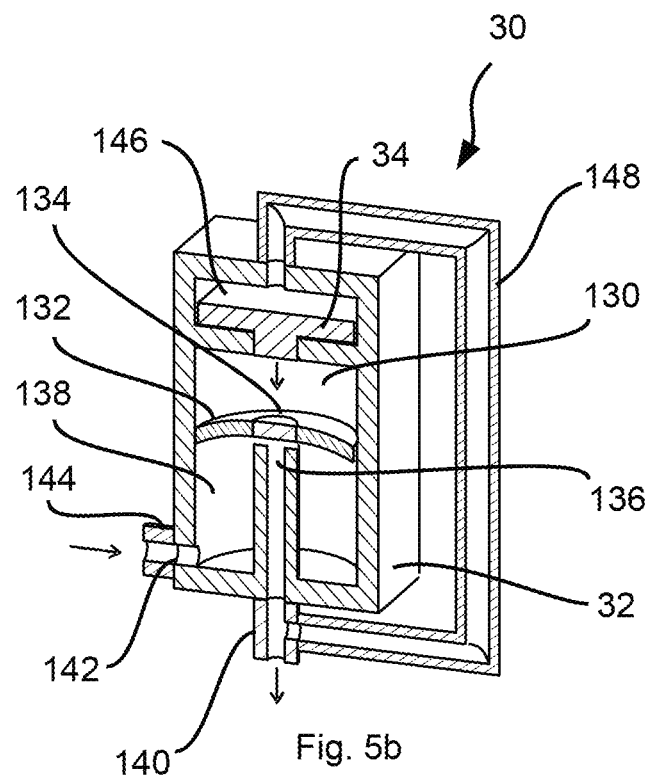
FIG. 5b is a sectional view of an alternative embodiment of a valve device according to FIG. 3.

The pneumatic valve device 30 according to FIG. 3 (FIGS. 3*a*, 3*b*) and FIG. 5 (FIGS. 5*a*, 5*b*; FIGS. 5*c*, 5*d*) can act as a proportional valve. Depending on how intensely the valve drive 34 is pumping, i.e., on how high the pressure is in the control pressure chamber 130, the distance between the closing element 134 and the first opening 136 can be controlled. In case of short distances, only a small fluid stream can flow from the first opening 136 to the second opening 142. In case of a great distance, i.e., at a low control pressure, a large fluid stream can flow between the first opening 136 and the second opening 142. In case of a function as a proportional valve, the pressure drag is kept at a constant value at the first opening 136.

The views in FIG. 5 (FIGS. 5*a*, 5*b* as well as FIGS. 5*c*, 5*d*) show a special embodiment of the valve device 30 according to FIG. 3. This valve device 30 may be used as an inhalation valve 26 in the patient module 20 (FIG. 2) and is controlled as a function of the back pressure. Here, the back pressure is the pressure that becomes established in the fluid flowing out of the pneumatic valve device 30. The admission pressure is correspondingly the pressure that becomes established during the flow into the pneumatic valve device 30. When—as is shown in FIG. 5*b*, the fluid flows from the second opening 142 to the first opening 136 with the closing element 134 opened, the state of admission pressure is present at the second opening 142 and at the pressure chamber 138 connected to the second opening 142. The back pressure is correspondingly present at the first opening 136 and at the first connection line element 140 connected thereto.

The embodiments according to FIG. 5 comprise first the same elements as does the embodiment according to FIG. 3, so that reference is made to the description given there. Concerning the flow direction through the valve device 30 according to FIGS. 5*a*, 5*b*, a flow direction reversed compared to the flow direction through the valve device 30 according to FIG. 3 is provided. Accordingly, the pressure source 14 (FIG. 1) may have been connected or is connected at the second connection line element 144 and the patient interface 10 (FIG. 1) may have been connected or is connected at least indirectly at the first connection line element 140.

In addition to the embodiment according to FIG. 3, the embodiment according to FIG. 5 comprises a connection chamber 146 belonging to the valve drive 34 and a branch line element 148 acting as a branch or connection line. A fluid is removed from the connection chamber 146 during the operation of the valve device 30 during a pumping operation and is pumped into the control pressure chamber 130 by means of the valve drive (piezo pump) 34.

Further, the connection chamber 146 is connected to the first connection line element 140 via the branch line element 148 in a fluid-communicating manner. A pressure equalization can thus take place via the branch line element 148 between the first connection line element 140 as well as the first opening 136 and the connection chamber 146. Thus, the back pressure prevails in the connection chamber 146.

When and as long as the valve drive 34 is switched on, a higher pressure prevails in the control pressure chamber 130 than in the pressure chamber 138 and at the first opening 136. The diaphragm element 132 is therefore pressed with the closing element 134 to the first opening 136 and it closes the first opening 136. A volume flow from the (inlet-side) second opening 142 to the (outlet-side) first opening 136 is not possible and a possible previous volume flow is interrupted.

As soon as the valve drive 34 is switched off, an open fluid-communicating connection becomes established between the control pressure chamber 130 and the connection chamber 146 (via the two-way duct 106; FIG. 3). A pressure equalization can thus take place between the connection chamber 146 and the control pressure chamber 130, so that the back pressure becomes established in the control pressure chamber 130. The same pressure is thus present in the control pressure chamber 130 as at the first opening 136 and as at the first connection line element 140.

Since the admission pressure in the pressure chamber 138 is higher than the back pressure due to the pressure source 14 connected at the second connection line element 144, the diaphragm element 132 is pushed with the closing element 134 into the control pressure chamber 130 (away from the first opening 136). The closing element 134 is thus moved into the opening state, so that the first opening 136 is opened. A fluid can thus flow between the (inlet-side) second opening 142 and the (outlet-side) first opening 136. In case of a functioning as an inhalation valve 26 in a patient module 20 according to FIG. 2, the pressure source 14 is connected to the second connection line element 144 leading to the second opening 142 and the first connection line element 140 joining the first opening 136 is open, for example, to the interior of the patient module 20 and thus indirectly to the patient interface 10 and to the airways of the patient or is connected to the patient interface 10.

FIG. 5*b* shows an operating state of the valve device 30, in which the valve drive 34 generates a pressure, which generates, together with the back pressure, a pressure in the control pressure chamber 130, which pressure causes the diaphragm element 132 and the closing element 134 to be deflected away from the first opening 136, so that a volume flow is possible from the second opening 142 to the first opening 136. The actuation of the valve device 30 consequently takes place in a back pressure-dependent manner.

The valve device 30 according to FIGS. 5*a*, 5*b* thus represents a back pressure-controlled pressure drag (the valve device 30 is a back pressure-controlled pressure drag/acts as a back pressure-controlled pressure drag). The opening state of the closing element 134 and the distance between the closing element 134 and the first opening 136 are controlled during the operation of the valve device 30 as a function of the back pressure. Depending on the value of the back pressure, the valve drive (piezo pump) 34 can pump only a certain volume into the control pressure chamber 130. When a low back pressure prevails, the control pressure will also be lower in the control pressure chamber 130 than when a higher back pressure would prevail. The distance between the closing element 134 and the first opening 136 is thus increased in case of a lower back pressure, because the diaphragm element 132 is pushed by the lower control pressure, which results from the lower back pressure, more deeply into the control pressure chamber 130 than in case of a higher back pressure.

Figure 5C:
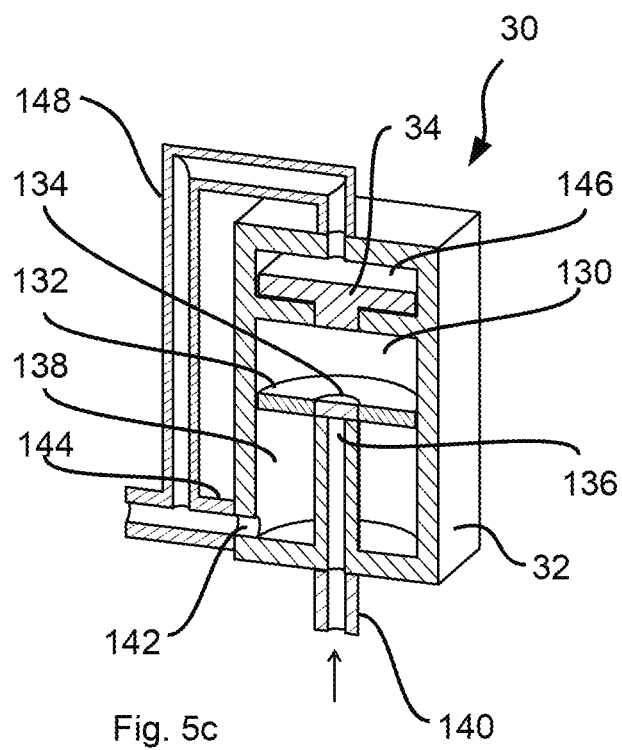
FIG. 5c is a sectional view of an alternative embodiment of a valve device according to FIG. 3.
Figure 5D:
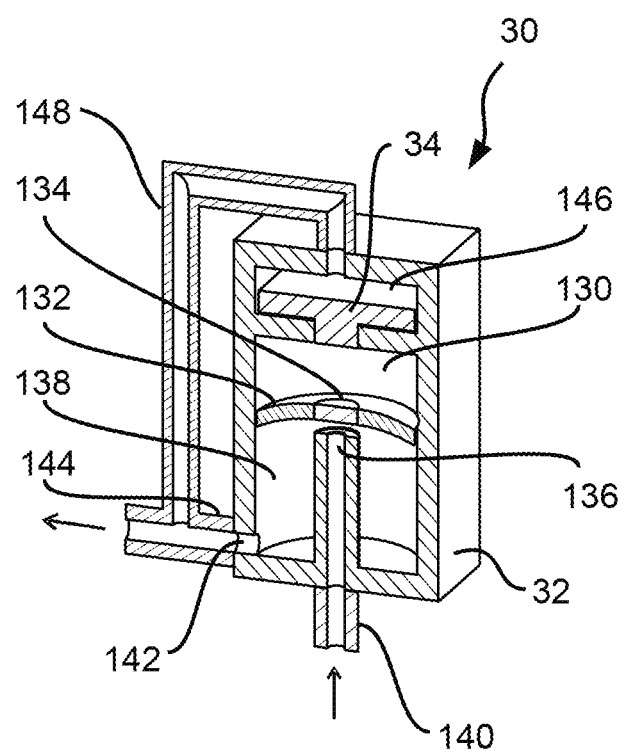
FIG. 5d is a sectional view of an alternative embodiment of a valve device according to FIG. 3.

The views in FIGS. 5c, 5d show another back pressure-controlled embodiment of the valve device 30. Unlike in the embodiment according to FIG. 5a, 5b, the pressure source 14 is or can be connected at the first connection line element 140 and at the second connection line element 144 (via the Y-piece) in such a valve device 30 (acting as an inhalation valve 26). Accordingly, the first connection line element 140 acts as an inlet and the second connection line element 144 as an outlet in this embodiment, as this is also indicated by the two arrows in the view shown in FIG. 5d. A volume flow through the valve device 30 from the (inlet-side) first connection line element 140 to the (outlet-side) second connection line element 144 is possible in the situation shown in FIG. 5d, and a back pressure control also takes place now by means of the patient-side (outlet-side) pressure.

Figure 6:
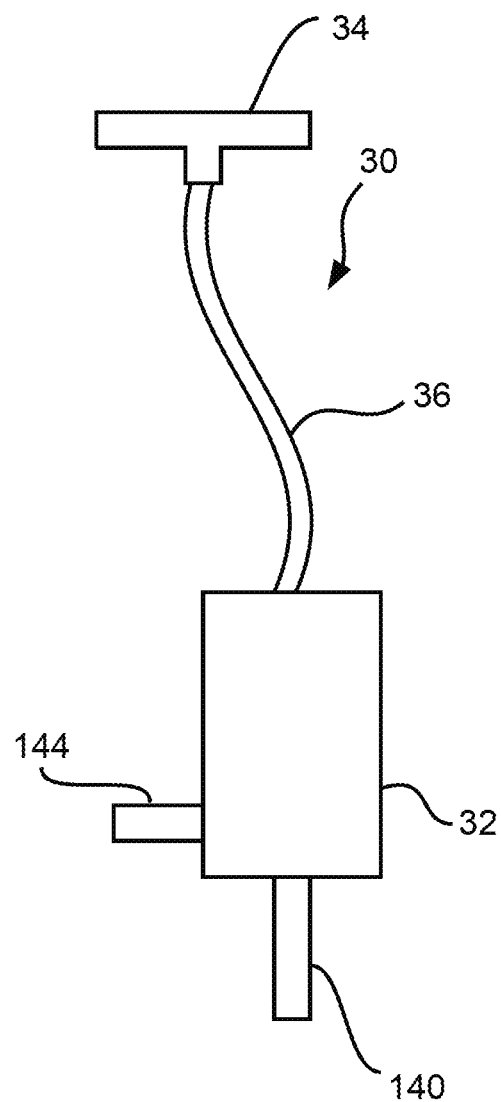
FIG. 6 is a schematic view of another alternative embodiment of a valve device according to FIG. 3 with a valve drive that can be arranged at a spaced location in space from the other elements of the valve device.

It applies to all valve devices 30 shown (FIG. 3, FIG. 5) that the valve drive 34 is—as is shown—either located within the housing 32 of the valve device 30 or can also be placed, as an alternative, outside the housing 32 and hence separated in space from the other components of the valve device 30. As this is shown in the view in FIG. 6 on the basis of the view in FIG. 3a and in a schematically highly simplified form, the valve drive 34 is connected now to the housing 32 of the valve device 30 by means of a connection in the form of a tube 36 or the like and the valve drive 34 is coupled with the control pressure chamber 130. The valve drive 34 is connected to the control pressure chamber 130 in a fluid-communicating manner for generating a control pressure in the control pressure chamber 130 in this case as well. This is correspondingly true of the embodiment according to FIG. 5, and the valve drive 34 is arranged now in a housing of its own (not shown), whose interior acts as a connection chamber 146, and the branch line element 148 opens in this case into the connection chamber 146, for example, in the form of an additional tube or the like.

FIG. 7 (FIGS. 7a through 7e) show the diaphragm element 132 and the closing element 134. For the sake of greater clarity, the reference numbers are shown in the view in FIG. 7a only. The diaphragm element 132 and the closing element 134 are located in the interior of the housing 32 of the valve device 30 and separate the control pressure chamber 130 from the pressure chamber 138.

Figure 7A:
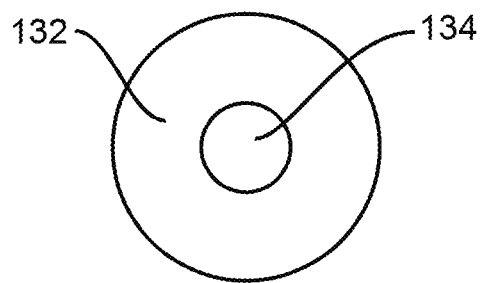
FIG. 7a is a schematic view of a diaphragm element and a closing element associated with the diaphragm element showing pressures acting on the different sides (underside or top side) and sections (diaphragm element or closing element)
Figure 7B:
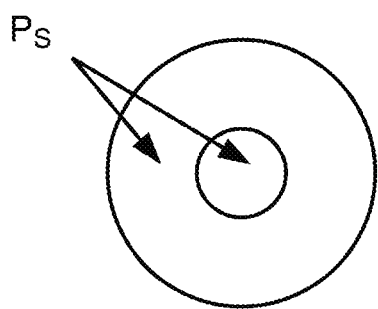
FIG. 7b is a schematic view of a diaphragm element and a closing element associated with the diaphragm element showing pressures acting on the different sides (underside or top side) and sections (diaphragm element or closing element)
Figure 7C:
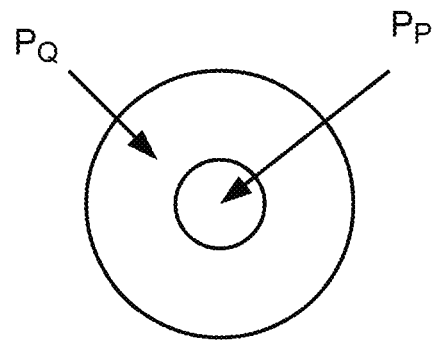
FIG. 7c is a schematic view of a diaphragm element and a closing element associated with the diaphragm element showing pressures acting on the different sides (underside or top side) and sections (diaphragm element or closing element)

The view in FIG. 7b shows the control pressure chamber-side (control pressure chamber 130) surface of the diaphragm element 132 (outside) and of the closing element 134 (inside) of the valve device 30 in FIGS. 5a, 5b. The control pressure $P_S$ from the control pressure chamber 130 is present here both in an outer area, i.e., at the diaphragm element 132, and in an inner area, i.e., at the closing element 134. The view in FIG. 7c shows the other, i.e., pressure chamber-side (pressure chamber 138) surface of the diaphragm element 132 and of the closing element 134 of the valve device 30 in FIGS. 5a, 5b. The pressure $P_Q$ of the pressure source connected to the second connection line element 144 is present on this side of the surface in the outer area, i.e., at the diaphragm element 132, and the patient-side pressure $P_P$ is present in the inner area, i.e., at the closing element 134.

Figure 7D:
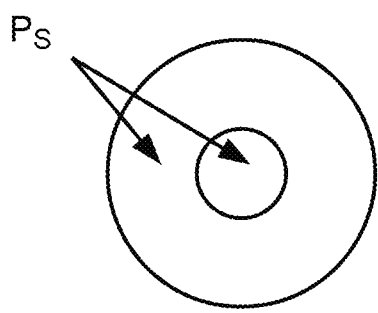
FIG. 7d is a schematic view of a diaphragm element and a closing element associated with the diaphragm element showing pressures acting on the different sides (underside or top side) and sections (diaphragm element or closing element)
Figure 7E:
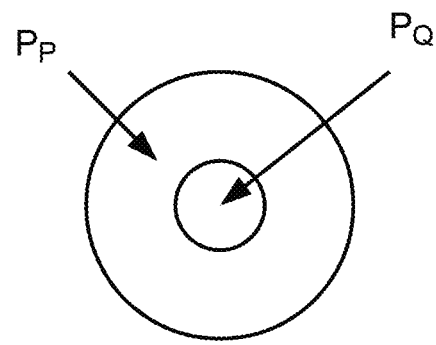
FIG. 7e is a schematic view of a diaphragm element and a closing element associated with the diaphragm element showing pressures acting on the different sides (underside or top side) and sections (diaphragm element or closing element)

The view in FIG. 7d shows the control pressure chamber-side surface of the diaphragm element 132 and of the closing element 134 of the valve device 30 in FIGS. 5c, 5d. The control pressure $P_S$ from the control pressure chamber 130 is present here both in an outer area, i.e., at the diaphragm element 132, and in an inner area, i.e., at the closing element 134. The view in FIG. 7e shows the pressure chamber-side surface of the diaphragm element 132 and of the closing element 134 of the valve device 30 in FIGS. 5c, 5d. The patient-side pressure $P_P$ is present on this side of the surface in the outer area, i.e., at the diaphragm element 132, and the pressure $P_Q$ of the pressure source connected to the second connection line element 144 is present in the inner area, i.e., at the closing element 134.

In a patient module 20 according to FIG. 2, this module comprises two valve devices 30, namely, a first valve device 30 acting as an inhalation valve 26 and a second valve device 30 acting as an exhalation valve 28, a respective corresponding valve drive 34 being arranged either likewise in the interior of the patient module 20 or also outside the patient module 20.

In a valve device 30 acting as an inhalation valve 26 according to FIG. 3, the ventilating tube 16 coming from the pressure source 14 is connected to the first connection line element 140 and the second connection line element 144 is connected via the Y-piece to the patient interface 10. In a valve device 30 acting as an exhalation valve 28 according to FIG. 3, the second connection line element 144 is open to the environment or a ventilation tube 18 open to the environment is connected to the second connection line element 144, while the first connection line element 140 is open to the interior of the patient module 20 or the first connection line element 140 is connected to the patient interface 10 via the Y-piece.

The patient module 20 comprises minimally exactly one valve device 30, namely, a valve device 30 acting as an exhalation valve 28. The valve drive 34 of the valve device 30 or of each valve device 30 may be located either in the interior of the patient module 20 or outside the patient module 20 and arranged there, for example, in a valve drive module that can be coupled with the patient module 20. In any case, the exhalation valve 28 opens to the environment and establishes a pressure equalization with the ambient pressure in the open state.

Figure 8:
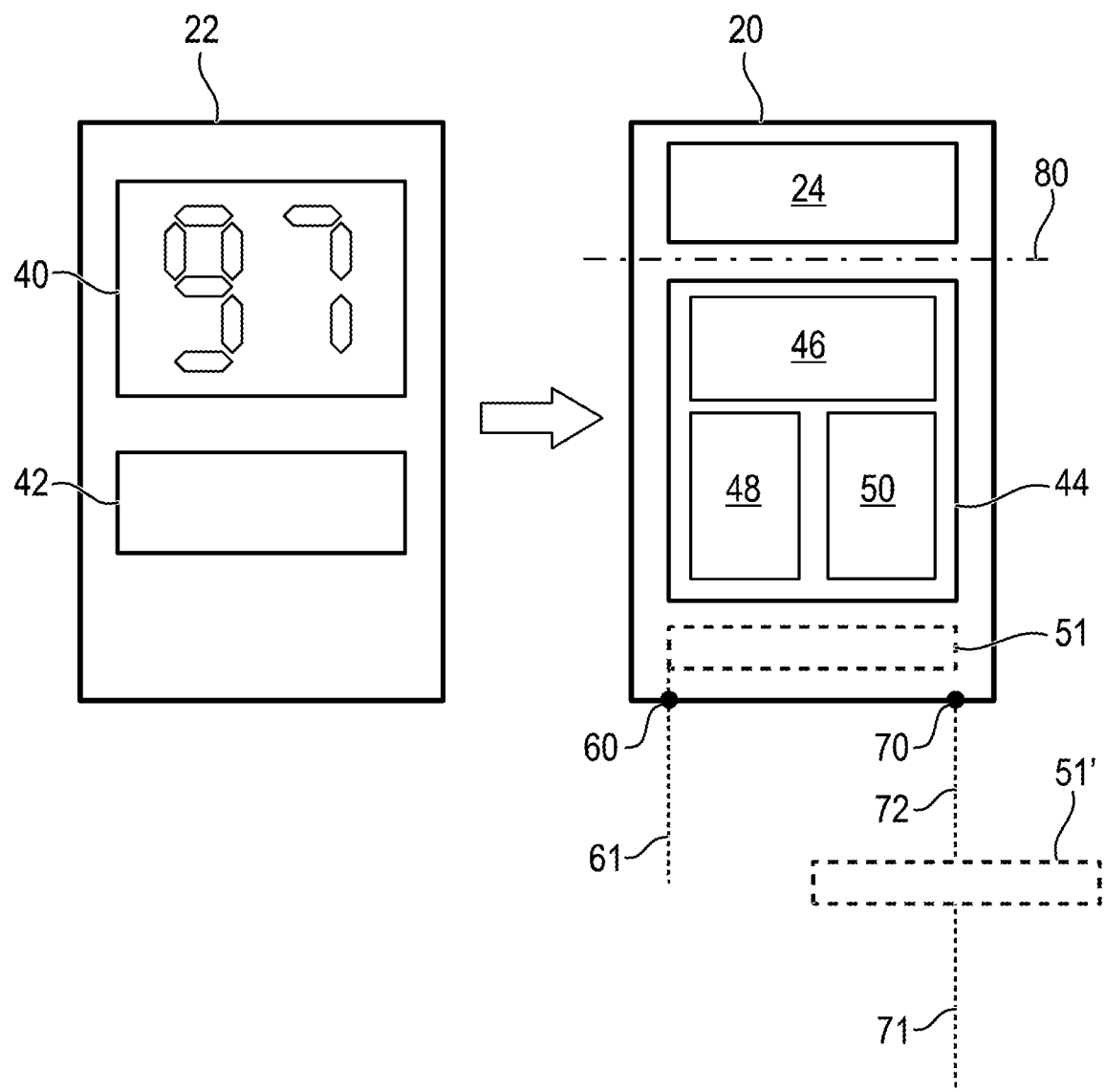
FIG. 8 is a schematic view of the patient module and an operating unit associated with the patient module.
Figure 9:
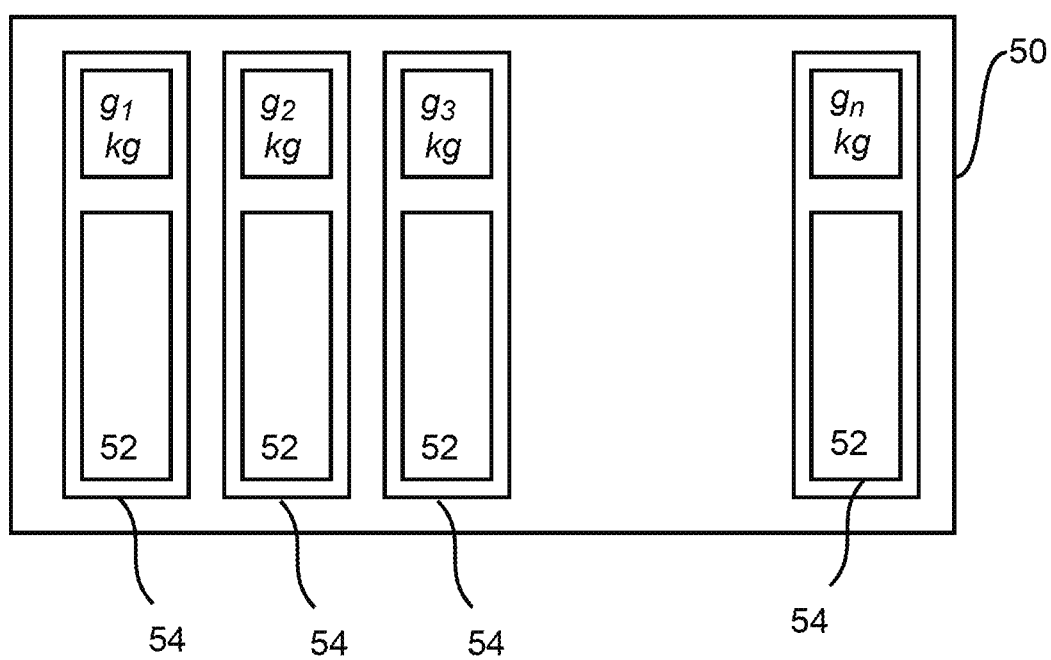
FIG. 9 is a schematic view of a lookup table as an example for an automatic determination of ventilation parameters by a patient module on the basis of a body weight value preset or presettable by means of an operating unit.

The view in FIG. 8 shows the operating unit 22 together with the patient module 20 with further details. Without abandoning a further general validity, an embodiment is shown here in which the operating unit 22 is independent from the patient module 20 and is connected to the patient module 20 in a communicating manner. The block arrow between the operating unit 22 and the patient module 20 represents a wired or wireless data transmission at least from the operating unit 22 to the patient module 20. In the embodiment shown as an example, the operating unit 22 comprises a display element 40 and an input element 42. The estimated body weight of the patient is inputted by means of the input element 42. The inputted body weight is displayed by means of the display element 40 for checking the input. The display element 40 may be eliminated in case of a corresponding input element 42, for example, in case of an input element 42 in the form of a rotary switch or the like, by means of which it is possible to select, for example, individual body weight values in 5-kg increments. The selected value can be recognized from the particular position of the input element 42 without a display element 40 as well.

A pressure and volume flow curve fitting the body weight value is automatically determined for the ventilation of the patient on the basis of the inputted body weight value (estimated body weight of the patient). This is carried out by means of a control unit 44, which may either be a part of the operating unit 22, a part of the patient module 20 or even independent from the operating unit 22 and the patient module 20. Without abandoning a further general validity, the following description will be continued on the basis of a control unit 44 comprised by the patient module 20.

In a manner known basically per se, the control unit 44 comprises a processing unit 46 in the form of or in the manner of a microprocessor as well as a memory, into which a computer program acting as a control program 48 is loaded. The control program 48 is executed during the operation of the patient module 20 by means of the processing unit 46 for ventilating the patient. The ventilation of the patient is carried out under the control of the control program 48 specifically basically in the known manner in the form of a control and/or regulation of the at least one valve device 30 comprised by the patient module 20 to obtain pressure and/or volume flow ratios for alternating phases of inhalation and exhalation. The patient module 20 comprises for this purpose the above-mentioned sensor mechanism 24, which comprises at least one pressure and/or flow sensor.

In reference to the innovation being proposed here, the control program 48 comprises computer program instructions for the interpretation of the datum or data that can be obtained from the operating unit 22 and code a body weight value. Based on the body weight value obtained, the control unit 44 determines ventilation parameters 52 (FIG. 4) fitting the body weight value, for example, on the basis of a lookup table 50 or the like. A lookup table 50 stored in the memory of the control unit 44 comprises for this purpose a plurality of data sets 54 with ventilation parameters 52, which data sets are associated with an individual body weight value or with a body weight value range. When accessing the lookup table 50, the data set 54 of the lookup table 50 best fitting the body weight value obtained from the operating unit 22 is selected in a manner basically known per se. The lookup table 50 comprises for this in each data set 54 in a manner known per se an index value (shown in the view in FIG. 8 as "g1 kg," "g2 kg," etc., wherein "g1," "g2," etc. indicate different weights or weight ranges), which makes it possible to select a data set 54 on the basis of the respective body weight value available from the operating unit 22. Interpretation is optionally performed in case of intermediate values. The ventilation of the patient and in this connection an actuation of the valve device 30 or of each valve device 30 comprised by the patient module 20, which actuation is basically known per se, is carried out with the ventilation parameters 52 of the determined data set 54 automatically and under the control of the control unit 44, namely, on the basis of the functionality of the patient module 20, which functionality is defined in the form of the control program 48.

Especially a tidal volume, a respiration rate, an inspiratory ventilation pressure, a pressure limitation and the so-called PEEP (positive end-expiratory pressure) belong to the ventilation parameters 52 comprised by each data set 54. Not all ventilation parameters 52 are necessarily dependent on the inputted body weight value and may thus be implemented as at least initial and body weight value-independent ventilation parameters. For example, at least one data set (not shown) with body weight value-independent ventilation parameters is then stored in the memory of the control unit 44, and the data sets 54 of the lookup table 50 comprise only body weight value-dependent ventilation parameters 52, especially the tidal volume as a ventilation parameter 52, which is obtained, for example, at 8 mL per kg of inputted body weight. The fact that it is possible, in principle, to calculate a body weight value-dependent ventilation 52 also shows that the weight-value-dependent ventilation parameter 52 or each body weight value-dependent ventilation parameter 52 can be calculated, as an alternative, by means of the processing unit 46 instead of a lookup table 50 or the like.

Figure 10:
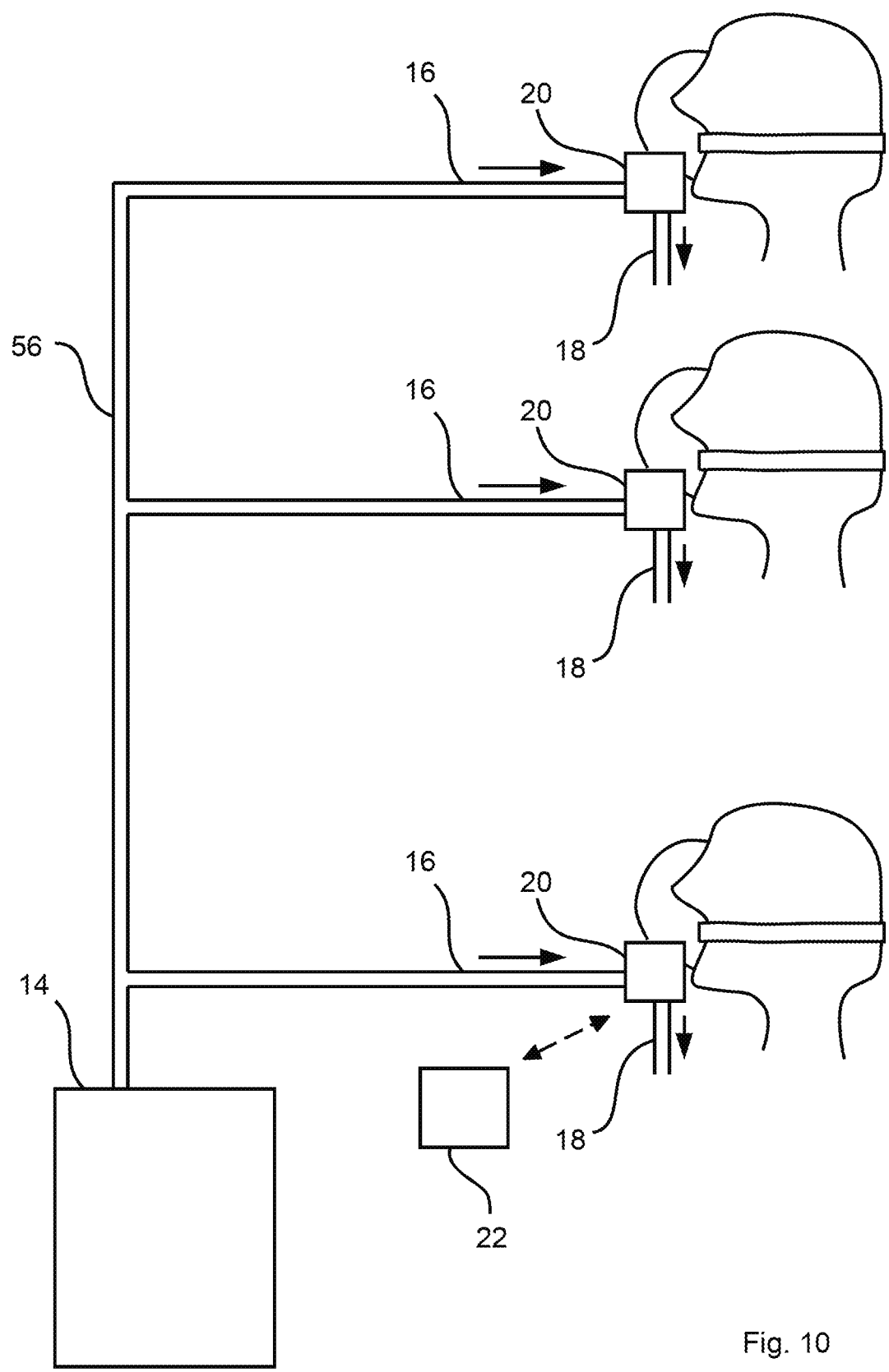
FIG. 10 is schematic view showing a system with a central pressure source and with a plurality of patient modules according to FIG. 1, FIG. 2 and FIG. 8, which are connected to the pressure source.

The view in FIG. 10 finally shows an embodiment in which a patient module 20 is connected for each patient at a central pressure source 14, for example, a compressor, especially a compressor with an O2 adsorber, for the simultaneous ventilation of a plurality of patients. The patient modules 20 are connected to the pressure source 14 by means of individual ventilation tubes 16 originating each as a stub line from a central line 56, possibly also from a line 56 in the form of a pipeline, so that each patient module 20 is supplied with the pressure of the pressure source 14 and with the volume flow originating from the pressure source 14. Based on the fact that identical or at least essentially identical conditions occur on the inlet side for each patient module 20, each patient module 20 consequently ensures on the outlet side, i.e., in the direction of the patient, the pressure and volume flow conditions necessary for the ventilation of the patient.

An arrangement according to FIG. 10 is advantageous if a plurality of patients are to be ventilated simultaneously. The possibility of a simple operation of each patient module 20 is found to be favorable here as well, since many responders can apply a face mask or the like and a patient module 20 to a plurality of patients simultaneously without a physician or other medically trained staff being present. Moreover, especially obvious is here the advantage that each patient module 20 acts as an interface between an inlet-side pressure source 14, especially a constant pressure source, and an outlet side and establishes the pressure and volume flow conditions necessary for the ventilation alone on the outlet side. Each patient module 20 operates independently and does not consequently require steady supervision.

A pressure source 14 and a plurality of patient modules 20 connected to it replace a plurality of ventilators otherwise necessary for a simultaneous ventilation of a plurality of patients in the scenario shown in FIG. 10. This leads to a greatly reduced amount of necessary devices, and a device suitable for use as a pressure source 14, especially a device that offers breathing gas under a pressure of, for example, 100 mbar and in which the breathing gas is generated by means of at least one compressor and at least one oxygen pressure swing adsorber, can be stocked together with a plurality of patient modules 20 in a markedly simpler manner than a corresponding plurality of ventilators.

It should be noted, in particular, that only one operating unit 22 is shown in the view in FIG. 10 for the plurality of patient modules 20. This represents a special case, but it does illustrate the possible reduction in terms of the number of devices, since a plurality of patient modules 20 can be set one after another with one operating unit 22 (presetting of the estimated body weight value) and/or be monitored. Such an operating unit 22 is then connected to a respective patient module 20 each preferably in a wireless manner, even though a wired connection to a respective patient module 20, established as needed, for example, by connecting a cable intended for the data transmission, comes into consideration as well.

The patient module 20 from FIG. 8 preferably has an electrical energy storage device 51. The electrical energy storage device 51 is, for example, a battery or a rechargeable electric battery for storing electrical energy.

The electrical energy storage device 51 is preferably located according to FIG. 8 within the patient module 20. The patient module 20 preferably has in this case an electrical interface 60, via which the electrical energy storage device 51 can be supplied with electrical energy by means of an electrical connecting line 61. The electrical energy storage device 51 provides electrical energy for the control unit 44 and preferably also for the sensors 24.

The electrical energy storage unit is preferably located outside the patient module 20 in the form of an electrical energy storage device 51' shown here rather than in the patient module 20. In this case, the electrical energy storage device 51' can then supply electrical energy for the control unit 44 and preferably also for the sensor mechanism 24 via an electrical connecting line 72 and an electrical interface 70 of the patient module 20. Further, the electrical energy storage device 51' is preferably configured to receive electrical energy via an electrical connecting line 71 for charging the electrical energy storage device 51'.

Contrary to the view shown in FIG. 8, it is possible that the control unit 44 is not located within the patient module 20 but outside the patient module 20. Provisions are preferably made in this connection for the control unit 44 to be located in a separate housing separately from a housing of the patient module 20. The electrical storage device 51 or 51' is preferably also located in this case in this separate housing together with the control unit 44. This separation, which is explained here, is shown in FIG. 8 by a separation limit in the sense of a module limit 80, which may also be considered to be a housing limit. The patient module 20 preferably also has now the sensor mechanism 24, but it is preferably connected to the control unit 44 and to the energy storage device 51, 51' via sensor lines not explicitly shown here.

The electrical energy storage unit 51, 51' shown in FIG. 8 preferably provides energy for the operation of the valve drive 34 shown in FIGS. 3 through 5 as well as 6.

The electrical energy storage unit 51, 51' is, for example, a rechargeable battery with a capacity of, for example, 10 Wh. If the energy needed for the actuation of the valve drive 34 were about 400 mW, operation would be possible for several hours.

Figure 11A:
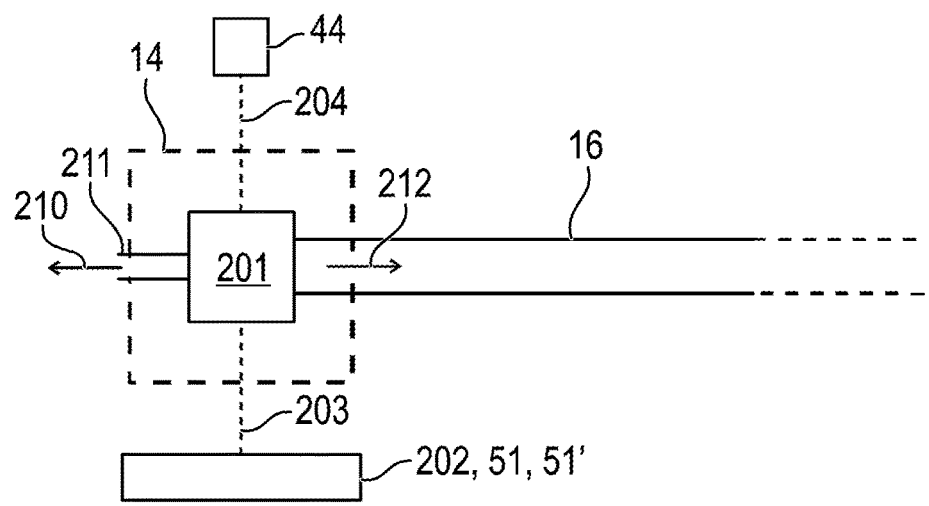
FIG. 11a is a schematic view showing one of preferred embodiments of pressure sources.

FIG. 11a shows a first exemplary embodiment of the pressure source 14, which is preferably a constant pressure source. The pressure source 14 is formed in this first exemplary embodiment by a gas feed unit 201, which is preferably a gas compressor unit or a blower. The gas feed unit 201 sucks in ambient air 210 via an inlet 211 and then provides compressed air 212 for the ventilation tube 16.

The gas feed unit 201 is connected to an electrical energy storage device 202 for operating the gas feed unit 201 via an electrical connection line 203. The electrical energy storage device 202 is preferably one of the electrical energy storage devices 51, 51' from FIG. 8.

The gas feed unit 201 is further connected to the control unit 44 from FIG. 8 via an electrical control line 204. As a result, the gas feed unit 201 can be actuated by the control unit 44 for reaching a certain pressure of the compressed air 212.

The gas feed unit 201 is consequently a unit that raises ambient air 210 to a higher pressure level. This higher pressure level preferably equals a desired ventilation inhalation peak pressure of, for example, 20 mbar. It is advantageous if the pressure of the compressed air 212 is higher than the necessary or desired ventilation inhalation peak pressure. Line resistances, for example, of the ventilation tube 16, can then be better compensated in this case.

The gas feed unit 201 has, for example, a power consumption of 6 W to 8 W. An energy storage unit 202 with a capacity of, for example, 10 Wh would be sufficient to operate the pressure source 14 for about 45 minutes until complete discharge of the energy storage device 202 if it would supply the control unit 44 with 400 mW. Operating times or a use time of about 20 minutes, which would be reached by the system being proposed here, are necessary in practice in the case of emergency equipment.

Figure 11B:
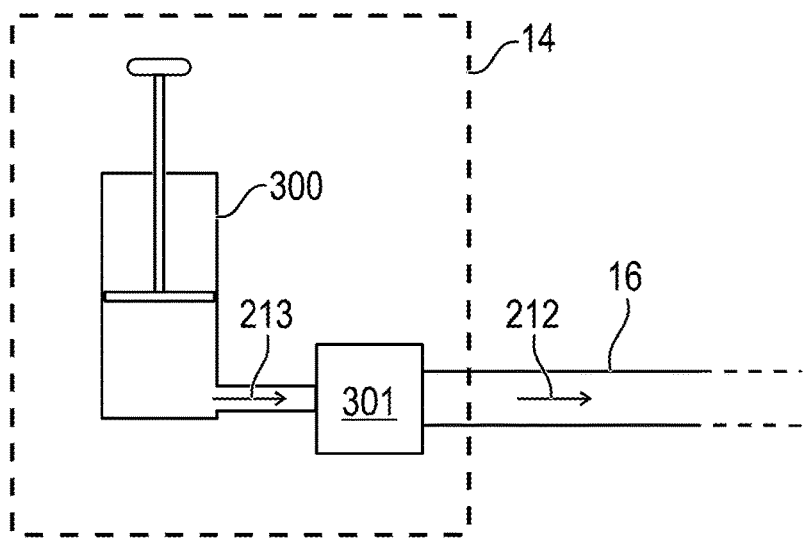
FIG. 11b is a schematic view showing another of preferred embodiments of pressure sources.
Figure 11C:
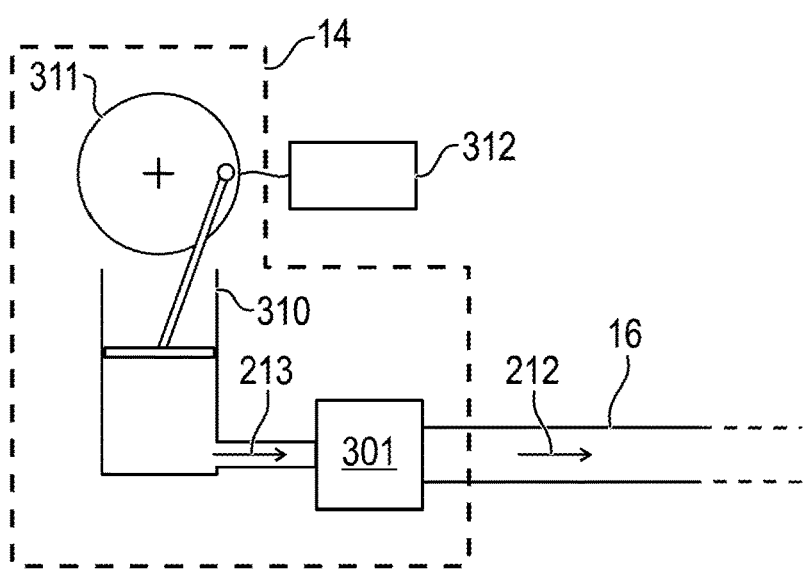
FIG. 11c is a schematic view showing another of preferred embodiments of pressure sources.

FIGS. 11b and 11c show other preferred exemplary embodiments of the pressure source 14. The compressed air 212 is provided in these exemplary embodiments shown in FIGS. 11b and 11c by means of a pressure-generating unit 300 or 310, 311, which can be actuated manually.

Further, a pressure storage unit 301, which stores compressed air potentials 213 generated by the manually actuatable pressure generation units and then provides compressed air 212, is preferably provided in the pressure source 14. This is advantageous because higher peak pressures, which are then stored intermediately in the pressure storage unit 301, can be generated by the manually actuatable pressure generation units 300 or 310, 311, so that it is possible to provide a compressed air 212 with a less variable or preferably constant pressure.

According to FIG. 11b, the manually actuatable pressure generation unit 300 is an air pump.

According to FIG. 11c, the manually actuatable pressure generation unit is a system comprising a piston 310 with a hand crank 311.

The pressure generation unit 300 or 310 consequently provides compressed air 213 for the pressure storage device 301, and this compressed air is then stored in the pressure storage unit 301 in a reservoir. The advantage of this is that the first responder does not have to continuously generate compressed air 213, but compressed air 212 can be taken from the pressure storage device 301 over longer periods of time after providing or generating compressed air 213 by the manually actuatable pressure generation unit 300 or 310, 311.

The pressure generation unit 301 preferably has a reservoir made of an elastic material, which is preferably similar to an air balloon. A uniform pressure curve of the compressed air 212 is guaranteed hereby.

Provisions are preferably made according to FIG. 11c for an electrical energy generation unit 312 to be mechanically coupled with the manually actuatable pressure generation unit 310, 311. The electrical energy generation unit 312 may be, for example, a generator, which is coupled with a hand wheel or a hand crank 311. The electrical energy generation unit 312 can then provide electrical energy for the electrical energy storage device 202 from FIG. 11a or 51, 51' from FIG. 8.

The pump 300 from FIG. 11b may preferably be a hand pump, a foot pump or another type of manual pump or a pump that can be operated by an operator.

The embodiments according to FIGS. 11b and 11c offer the advantage that the operating time of the ventilator or ventilation system is also possible in cases of emergency during which the operating time exceeds the period of 20 minutes.

The compressed air 212 from FIGS. 11a, b, c as well as 12 advantageously has a pressure of 50 mbar.

Figure 12:
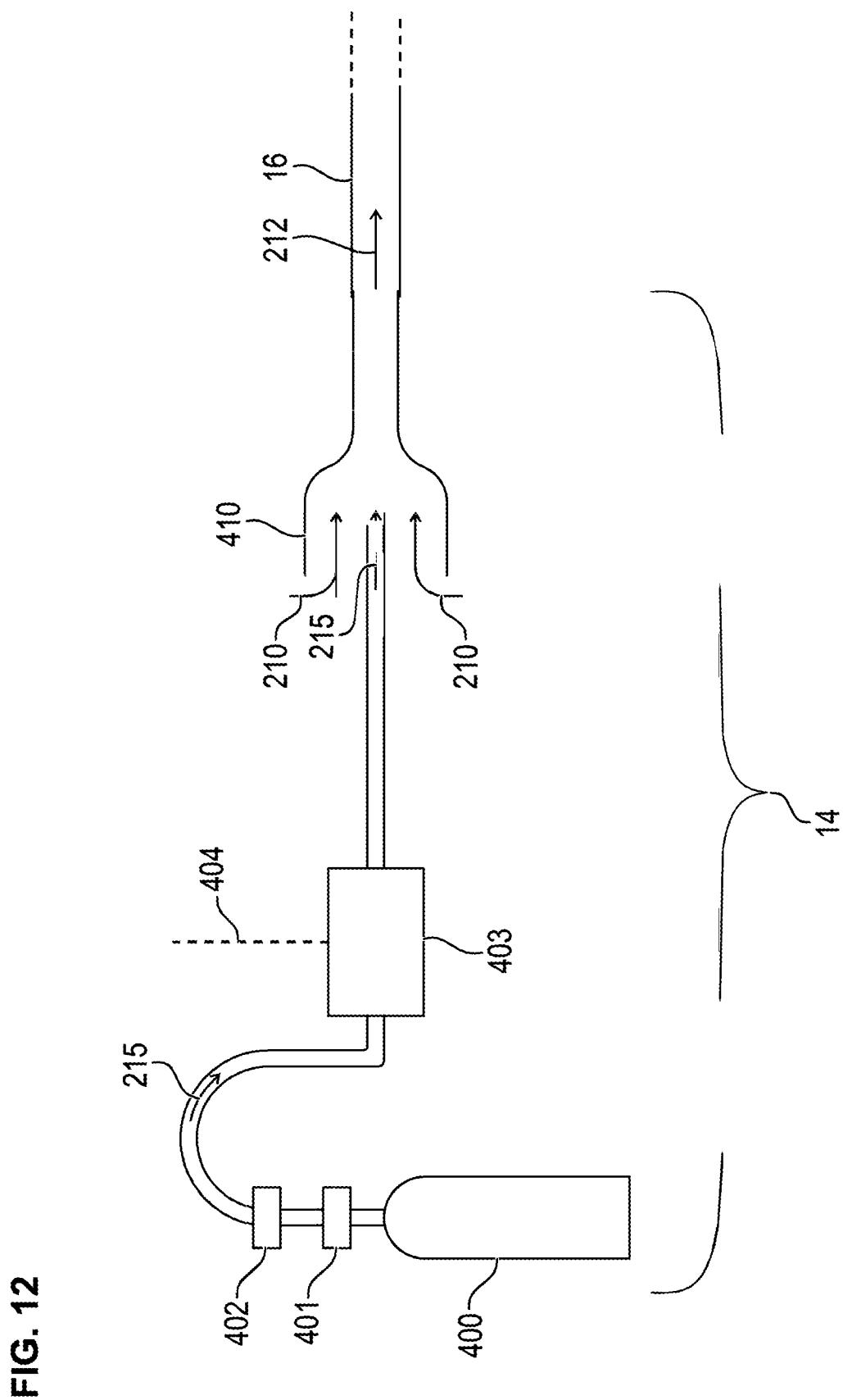
FIG. 12 is a schematic view showing another preferred embodiment of a pressure source.

FIG. 12 shows another preferred embodiment of the pressure source 14 for providing compressed air 212 for the ventilation tube 16.

The pressure source 14 has a pressure storage source 400, which is preferably a compressed air cylinder or gas cylinder. A valve 401, which controls a pressure potential of the unit 400, is preferably provided, so that the flow of air from the unit 400 can be controlled hereby. The valve 401 is preferably a valve that can be actuated manually by a user.

Further, a so-called pressure reducer 402 is preferably provided in order to change the pressure potential present at the pressure reducer 402 to a lower pressure. A pressure potential of 50 mbar is preferably present behind the pressure reducer 402.

The compressed air of the unit 400 provided behind the pressure reducer 402 can then preferably be made available for the ventilation tube 16 as the compressed air 212.

It is possible as an alternative that the compressed air 215 provided from the unit 400 by means of the pressure reducer 402 is enriched with ambient air 210 by means of an ejector 410.

Mixing of the compressed air 214 from the unit 400 with the ambient air 210 takes place as a result.

The advantage is that a lower gas consumption can be made possible hereby from the unit 400 at equal gas consumption of the compressed air 212 from the ventilation tube 16. For example, a provision of compressed air 212 can be made possible hereby over a longer time period.

If the unit 400 provides, for example, oxygen as the compressed air 215, it is possible to provide four times the amount of compressed air 212 in the case of a mixing ratio of 25% of compressed air 215 to 75% of ambient air 210 compared to the case in which the ejector 410 is not provided.

The pressure source 14 preferably comprises a generator unit 403, which generates electrical energy from the compressed air 215 of the unit 400. This electrical energy of the electrical energy generation unit 403 can then be made available via an electrical line 404. This is advantageous because electrical energy can be provided hereby via the electrical line 404 for the electrical energy storage device 202 from FIG. 11a or for an electrical energy storage device 51, 51' according to FIG. 8, so that the electrical energy of the storage device 51, 51', 202, which energy is present at the initial operating time, does not represent as a result a limitation, but more electrical energy can be generated by means of the compressed air 215 of unit 400.

The electrical energy generation unit 403 preferably has a turbine for generating electrical energy from the compressed air 215. As an alternative, the electrical energy generation unit 403 preferably has a piston unit together with a generator for generating electrical energy from the compressed air 215.

Individual key aspects of the description being submitted here can thus be briefly summarized as follows: Proposed are a process for ventilating a patient as well as a device, which operates according to the process and is called a patient module 20 here, wherein at least one estimated value concerning a biometric feature of the patient, namely, a body weight value concerning an estimated body weight of the patient, and/or a length value of an estimated body weight of the patient, can be transmitted to a patient module 20 intended for ventilating the patient, and is transmitted during the operation, wherein the patient module 20 automatically selects ventilation parameters 52 fitting the estimated value on the basis of the at least one estimated value or on the basis of an estimated value, and wherein the ventilation of the patient is carried out with the selected ventilation parameters 52.

While specific embodiments of the invention have been shown and described in detail to illustrate the application of the principles of the invention, it will be understood that the invention may be embodied otherwise without departing from such principles.

The invention claimed is:

1. A device for ventilating a patient, the device comprising:
a pressure source coupling for flow to a patient interface, which can be connected to the airways of a patient, and the device can be detachably connected to the patient interface;
a valve device either acting as an exhalation valve or acting as an inhalation valve, the valve device comprising a diaphragm element having a closing element, a valve drive, a pressure chamber and a control pressure chamber, wherein the valve drive is fluid communicatingly connected to the control pressure chamber for generating a control pressure in the control pressure chamber, wherein the control pressure chamber is separated from the pressure chamber by means of the diaphragm element having the closing element, wherein a first opening of the pressure chamber is opened and closed by means of the closing element and the closing element is controlled via the diaphragm element by means of the control pressure, and wherein a piezo pump acts as the valve drive, wherein the valve device when acting as the inhalation valve comprises a connection chamber belonging to the valve drive as well as a branch line element fluid communicatingly connecting the connection chamber to an outlet-side connection line element,
wherein the valve device comprises a length and a longitudinal axis that extends along the length of the valve device; wherein the closing element is axially opposite the first opening with respect to the longitudinal axis of the valve device; and
a processing unit configured to:
receive a transmission of an estimated value concerning an estimated biometric feature of the patient, wherein a body weight value concerning an estimated body weight of the patient and/or a length value concerning an estimate height of the patient are received as the estimated value concerning a biometric feature of the patient;
automatically select ventilation parameters fitting the estimated value on the basis of the estimated value; and
select, for carrying out the ventilation of the patient by means of the device, ventilation parameters.

2. A device in accordance with claim 1, wherein the processing unit is associated with a storage device, into which a computer program is loaded, wherein the computer program is executed during operation of the device by the processing unit.

3. A device in accordance with claim 1, wherein the connection chamber is located between the piezo pump and an outlet of the branch line element when the valve device acts as the inhalation valve.

4. A device in accordance with claim 1, wherein a portion of a housing of the piezo pump defines a portion of the connection chamber when the valve device acts as the inhalation valve.

5. A device in accordance with claim 1, wherein the closing element comprises a planar closing element surface, the first opening being defined by a portion of a housing of the valve device extending in the pressure chamber, the portion of the housing comprising a housing planar surface, the closing element surface being in contact with the housing planar surface when the first opening is closed via the closing element.

* * * * *